US008871966B2

(12) United States Patent
Kraus et al.

(10) Patent No.: US 8,871,966 B2
(45) Date of Patent: Oct. 28, 2014

(54) REGIOSPECIFIC SYNTHESIS OF TEREPHTHALATES

(71) Applicants: George A. Kraus, Ames, IA (US); Jennifer J. Lee, Ames, IA (US)

(72) Inventors: George A. Kraus, Ames, IA (US); Jennifer J. Lee, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 13/840,768

(22) Filed: Mar. 15, 2013

(65) Prior Publication Data

US 2014/0275608 A1    Sep. 18, 2014

(51) Int. Cl.
*C07C 69/67* (2006.01)
*C07C 67/00* (2006.01)

(52) U.S. Cl.
CPC ............................... *C07C 67/00* (2013.01)
USPC ....................................................... 560/96

(58) Field of Classification Search
CPC .......... C07C 63/26; C07C 69/82; C07C 69/80
USPC ............................................. 560/84, 85, 96
See application file for complete search history.

(56) References Cited

U.S. PATENT DOCUMENTS 7,385,081 B1   6/2008   Gong

FOREIGN PATENT DOCUMENTS

WO    WO-2009064515 A1    5/2009
WO    WO-2009105500 A1    8/2009
WO    WO-2013015918 A1    1/2013

OTHER PUBLICATIONS

Afarinkia et al. (Diels-Alder Cycloadditions of 2-Pyrones and 2-Pyridones, Tetrahedron vol. 48, No. 42, pp. 9111-9171, 1982).*
"International Application Serial No. PCT/US2012/043580, International Preliminary Report on Patentability mailed Feb. 6, 2014", 5 pgs.
"International Application Serial No. PCT/US2012/043580, Search Report mailed Sep. 13, 2012", 4 pgs.
"International Application Serial No. PCT/US2012/043580, Written Opinion mailed Sep. 13, 2012", 3 pgs.
Afarinkia, K., et al., "Diels-Alder cycloadditions of 2-pyrones and 2-pyridones", Tetrahedron, 48(42), (1992), 9111-9171.
Amatore, Muriel, et al., "Synthesis of functionalised diarylmethanes via a cobalt-catalysed cross-coupling of arylzinc species with benzyl chlorides", Chem. Commun., 40, (2008), 5019-5021.
Ashworth, I. W, et al., "A New Route for Manufacture of 3-Cyano-1-naphthalenecarboxylic Acid", Org. Proc. Res. Dev., 7(1), (2003), 74-81.
Bryson, T. A, et al., "Diels-Alder synthesis of hindered aromatic amines", J. Org. Chem., 42(17), (1977), 2930-2931.
Delaney, P. M, et al., "A 2-pyrone cycloaddition route to functionalised aromatic boronic esters", Tetrahedron, 64(5), (Jan. 28, 2008), 866-873.
Kraus, George A, et al., "Aromatics from pyrones: para-substituted alkyl benzoates from alkenes, coumalic acid and methyl coumalate", Green Chemistry, 13(10), (Aug. 22, 2011), 2734-2736.
Kraus, George A, "Chapter 10: Phytochemicals, Dyes, and Pigments in the Biorefinery Context", Biorefineries-Industrial Processes and Products, Wiley-VCH Verlag GmbH, (2006), 315-324.
Kraus, George A, "Synthetic Methods for the Preparation of 1,3-Propanediol", CLEAN—Soil, Air, Water, 36(8), (Aug. 2008), 648-651.
Leijondahl, Karin, et al., "Enantiopure 1,5-Diols from Dynamic Kinetic Asymmetric Transformation. Useful Synthetic Intermediates for the Preparation of Chiral Heterocycles", Org. Lett.,10(10), (2008), 2027-2030.
Matsushita, Yoh-Ichi, et al., "A Convenient Synthesis of Methyl 4-Substituted Via Diels-Alder Reaction in the Presence of Palladiumb on Activated Carbon", Synthetic Communications, 24(22), (1994), 3307-3313.
Pratt, Andrew J, et al., "Thermal Decomposition of 1,1-bis(methylthio)ethene, Pyran-2-one Diels-Alder Adducts", An Unusual [1,5]-Sulfenyl Rearrangement. Arkivoc, [online] URL=<http://www.arkat-usa.org/get-file/19778/>, (2006), 211-212.
Savard, Jacques, et al., "Reactions of ketene acetals-14 the use of simple mixed vinylketene acetals in the annulation of quinones", Tetrahedron, 40(18), (1984), 3455-3464.
Sheehan, Richard J, "Terephthalic Acid, Dimethyl Terephthalate, and Isophthalic Acid", Ullmann's Encyclopedia of Industrial Chemistry, (Jun. 15, 2000), 21 pgs.
Viehe, Heinz G, et al., "The captodative effect", Acc. Chem. Res., 18(5), (1985), 148-154.
Zeitsch, Karl J, "Chapter 16. Diacetyl and 2,3-Pentanedione", The Chemistry and Technology of Furfural and its Many By-Products, Amsterdam ; New York : Elsevier, (2000), 137.

* cited by examiner

*Primary Examiner* — Brandon Fetterolf
*Assistant Examiner* — Blaine G Doletski
(74) *Attorney, Agent, or Firm* — Schwegman Lundberg & Woessner, P.A.

(57) ABSTRACT

A method for preparing 1,4-biscarboxylic acid esters of benzene is provided.

11 Claims, No Drawings

REGIOSPECIFIC SYNTHESIS OF TEREPHTHALATES

STATEMENT OF GOVERNMENT GRANT SUPPORT

This invention was made with the support of the Department of Commerce under Grant no. 057905210i6 and with the support of the National Science Foundation under Grant no. EEC0813570. The U.S. Government has certain rights in this invention.

BACKGROUND

The development of new, cost-competitive processes that utilize renewable resources as feedstocks is vital for a sustainable economy. These processes also represent important milestones toward the goal of reducing the United States' dependence on foreign oil. Introduction of such processes not only avoids the use of more petroleum, but also has the potential to provide substantial energy savings, and reduce greenhouse gas emissions. Although biobased syntheses of certain commercially significant compounds such as 1,3-propanediol have been reported, there are comparatively few reported approaches to compounds related to terephthalic acid. See, e.g., G. A. Kraus, Clean—Soil, Air, Water, 36, 648 (2008); W. H. Gong (BP Corporation N. A., Inc.), PCT WO 09/064,515; WO 08/63703; U.S. Ser. No. 07/940,097).

Terephthacidic acid, or 1,4-biscarboxybenzene is a precursor for the widely used polyester PET, used to make clothing and plastic bottles. Terephthalic acid is currently produced by the oxidation of para-xylene in air using cobalt and manganese salts to catalyze the reaction.

The Diels-Alder reaction of pyrones such as coumalic esters with activated alkynes has been described. See, e.g, K. Afarinka et al., Tetrahedron, 48, 9111 (1992) and T. A. Bryson et al., J. Org. Chem., 42, 2930 (1977). As shown in Scheme 1, wherein A is an activating group, the reaction of alkynes with methyl coumalate (1) involves a cycloaddition to produce bicyclo[2.2.2]octadiene intermediate 2 that loses carbon dioxide to directly form the substituted benzene. Delaney et al., have utilized this reaction to produce phenols. P. M. Delaney et al., Tetrahedron, 64, 866 (2007).

The reaction of activated alkenes, such as acrylates or acrylonitrile, with methyl coumalate produces bicyclic lactone 3, wherein A is an alkoxycarbonyl or CN, that cannot go directly to an aromatic ring by loss of carbon dioxide. One way to construct aromatic rings via this intermediate is to catalytically dehydrogenate adduct 3 under conditions that lead to loss of carbon dioxide. Y. Matsushita et al., Synth. Commun., 24, 3307 (1994).

Scheme 1: Diels-Alder Reaction with Activated Alkynes and Alkenes

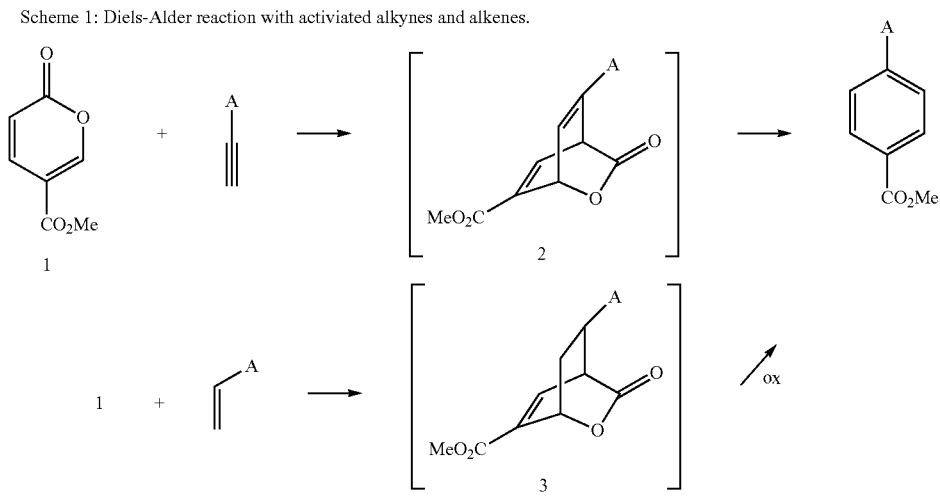

The reaction of unactivated alkenes with pyrones can also afford high yields of aromatic products if a dehydrogenation catalyst is present. This strategy has been used to generate a number of para-substituted benzoic acids, as shown below in Scheme 2, wherein R is alkyl. See, G. A. Kraus et al., Green Chem., 13, 2734 (2011). Although alkenes such as alpha-olefins react with 1 with high regio selectivity, acrylates react with 1 to generate a mixture of terephthalates and isophthalates with poor regioselectivity.

Scheme 2. Diels-Alder Reaction with Unactivated Alkenes

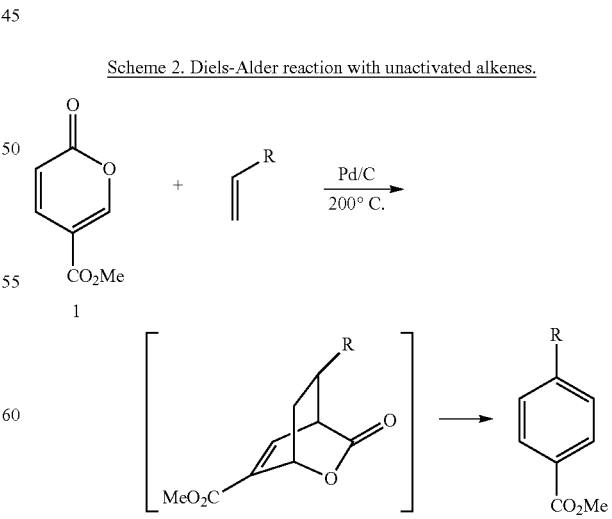

Since the seminal work of Viehe, alkenes bearing an electron-withdrawing group and an electron-donating group on the same carbon (captodative alkenes) can exhibit excellent regioselectivity in radical addition reactions, 1,3-dipolar cycloaddition reactions and the Diels-Alder reactions. See, H. G. Viehe et al., *Acc. Chem. Res.*, 18, 148 (1985). However, captodative alkenes have not been reported to react with pyrones. Therefore, while both electron-rich alkenes such as vinyl ethers and electron-deficient alkenes such as acrylonitrile can react with pyrones, a need exists for an efficient route to terephthlates employing captodative alkenes.

SUMMARY OF THE INVENTION

The invention provides, in various embodiments, a method of synthesis of a compound of formula (I):

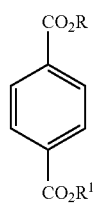
(I)

wherein each R and $R^1$ is individually selected from H, alkyl, aryl, arylalkyl, cycloalkyl or cycloalkylalkyl, by reaction of a coumalate compound of formula (II):

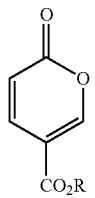
(II)

optionally in the presence of a solvent, with a captodative alkene of formula (III), (IV) or (V):

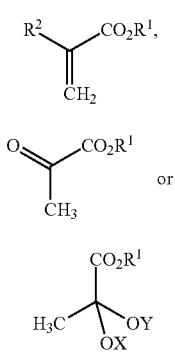
(III)
(IV)
(V)

wherein $R^2$ is —OR, —SR, halo (F, Cl, Br, I), $(R)_2N$, RC(O)—, or —O[Si $(R^a)(R^b)(R^c)$] wherein each of $R^a$, $R^b$ or $R^c$ are selected from $(C_1$-$C_6)$alkyl, and wherein X and Y are R or $R^1$ or together are —$(CH_2)_n$—, wherein n is 2-3 and —$(CH_2)_n$— is optionally substituted with R, to yield a compound of formula (I). Preferably N(R)(R) is R(H)N. Preferably R is $(C_1$-$C_6)$alkyl, e.g., $(C_1$-$C_4)$alkyl.

It is believed that compound (IV) functions as a precursor of enol (III), wherein $R^2$ is OH, in the reaction. Preferably, R, $R^1$, $R^2$, X and Y are $(C_1$-$C_4)$alkyl, most preferably methyl, so that the compound of formula (I) is dimethyl terephthalate. The diester is readily convertible to terephthalic acid.

This route has advantages over the route shown in Scheme 2. First, the palladium on carbon catalyst for dehydrogenation is not required. Second, the diester functionality is produced directly without the need for a benzylic oxidation (unnecessary oxidation of A in Scheme 1). The methanol by-product produced in the reaction will be recyclable. Either ketal V ($R^1$, R, X and Y are methyl) or methyl pyruvate can be produced from pyruvic acid and methanol in one step.

An outstanding advantage of the present method is that the product resulting from contacting the coumalate compound of formula (II) and the alkene of formula (III) is substantially free of a regiomeric meta-substituted benzoate impurity 5 of formula:

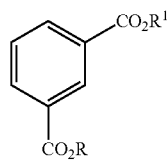

As shown in Scheme 3, below, two theoretical intermediates, 6 and 7, can be envisioned, yet only the para-substituted product 4 and not the meta-substituted 5 is detected in significant quantities in the reaction product. When a coumalate ester is used, such as methyl coumalate, the yield of the para-methoxycarbonyl-substituted benzoate can be at least about 50%, and can also range upwards to greater than about 80%.

Scheme 3: Possible Regiomeric Outcomes from
Diels-Alder Reaction of Methyl Coumalate with
Alkenes of Formula (III)

Scheme 3: Possible regiomeric outcomes from Diels-Alder reaction of methyl coumalate with alkenes of formula (III).

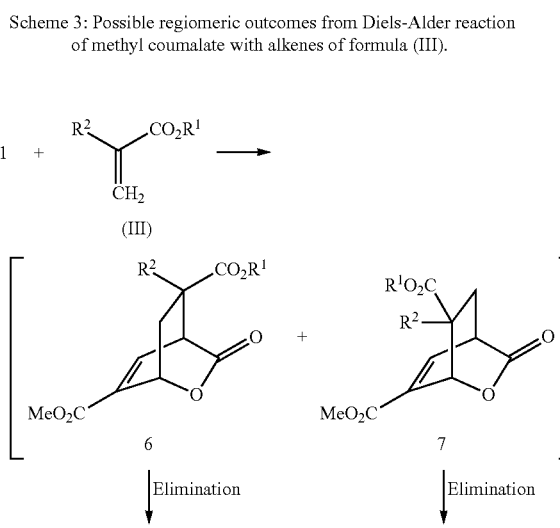

-continued

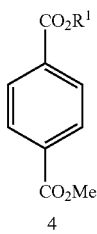
4

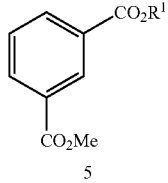
5

As the results in Table 1 indicate, only the para-substituted adduct 4 was produced, as evidenced by the proton NMR.

In other embodiments, R and $R^1$ are H. Coumalic acid in free form has been found to undergo the same regioselective Diels-Alder cycloaddition to selectively provide the para-benzoate product, i.e., the para-carboxy-substituted benzoic acid. The mono- or di-carboxylic acid can be then esterified to yield the diester.

In various embodiments, a method of the invention further comprises conversion of the terephthalate to a polyester polymer by condensation of the terephthalate with a diol. For example, condensation of the terephthalate with ethylene glycol can be used to produce polyethyleneterephthalate or condensation of the terephthalate with butylene glycol can be used to produce polybutyleneterephthalate. Again, due to the high regioselectivity for production of the para-substituted compound by the inventive process, the terephthalate-containing polymer is substantially free of isophthalate moieties.

In various embodiments, the reaction conditions can comprise contacting the coumalate compound of formula (II) with (III), (IV) and/or (V). The reaction can be carried out at molar ratio of (II):(III), (IV) and/or (V) of about 1:1-4, preferably above 1:1.5-3 at an elevated temperature, neat or optionally in a solvent. For example, the elevated temperature can be about 125° C. to 250° C., e.g., 150° C. to 200° C., and the reaction time can be about 3-16 hrs. Although the reaction can be carried out in a neat melt, the contacting can also be carried out in a solvent, such as a hydrocarbon, of a boiling point of not less than about 100° C. For example, the solvent can comprise mesitylene or toluene, high boiling aromatic hydrocarbons. When coumalic acid is used, solubility in mesitylene is not as great as is the solubility of methyl coumalate, but the acid goes into solution in mesitylene at effective concentrations of about 140° C. or higher.

The reaction product can be readily purified by cooling the reaction vessel to room temperature, then rinsing the vessel with ethyl acetate. The resulting solution can then be concentrated and purified by recrystallization (e.g., from hexanes).

DETAILED DESCRIPTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

Phrases such as "under conditions so as to provide," "to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

Alkyl groups include straight chain and branched alkyl groups and cycloalkyl groups having from 1 to about 20 carbon atoms, and typically from 1 to 12 carbons or, in some embodiments, from 1 to 8 or 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups.

As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups or arylalkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The invention will be further described by reference to the following detailed examples, wherein 2,2-dimethoxypropanoate (11) and 2-methoxyacrylate (10) were prepared according to the following patent: Cooper et al., (Schering Corp., USA) PCT/US 09/34447, Feb. 19, 2009.

Example 1

Synthesis of dimethyl terephthalate via methyl 2-((trimethylsilyl)oxy)acrylate

The synthesis of dimethyl terephthalate (9) via methyl 2-((trimethylsilyl)oxy)acrylate (8), prepared in accord with Leijohdahl et al., Org. Lett., 10, 2027 (2008), is representative. To a sealable tube flushed with argon was added methyl coumalate (1) (154 mg, 1.0 mmol), followed by 8 as a crude mixture (261 mg, 1.5 mmol). The mixture was heated to 200° C. for 16 hours, after which it was cooled to room temperature. The resulting crude mixture was recrystallized from hexanes to afford 9 (165 mg, 85%) as a white crystalline solid: $^1$H NMR (CDCl$_3$, 400 MHz) δ=8.10 (s, 4H), 3.95 (s, 6H) ppm; $^{13}$C NMR (CDCl$_3$, 100 MHz) δ=166.4, 134.1, 129.7, 52.6 ppm.

Example 2

Optimization Trials for dimethyl terephthalate via methyl 2-((trimethylsilyl)oxy)acrylate

TABLE 1

| Entry | Temperature (° C.) | Time (h) | Equivalents of 8 | Concentration (M) | Ratio of 9:8[a] |
|---|---|---|---|---|---|
| 1 | 200 | 17 | 1.5 | 0.5 | 1:0.53 |
| 2 | 200 | 16 | 3.0 | 0.5 | 1:0 |
| 3 | 150 | 18 | 3.0 | 0.5 | 1:0.48 |
| 4 | 100 | 17 | 3.0 | 0.5 | 1:4.00 |
| 5 | 150 | 16 | 3.0 | Neat | 1:0 |
| 6 | 100 | 16 | 3.0 | Neat | No 9 formation |
| 7 | 150 | 16 | 1.5 | Neat | 1:0.12 |
| 8 | 150 | 17 | 1.0 | Neat | 1:1.12 |
| 9 | 125 | 18 | 1.5 | Neat | 1:0.72 |
| 10 | 150 | 6 | 1.5 | Neat | 1:0.50 |
| 11 | 150 | 3 | 3.0 | Neat | 1:0.49 |
| 12 | 150 | 1 | 1.5 | Neat | 1:1.31 |

[a]Ratios determined by integration of crude $^1$H NMR.

Example 3

Synthesis of dimethyl terephthalate via 2-methoxyacrylate

The experimental procedure to synthesize 9 was followed as described in Example 1; however, the reaction was maintained at 200° C. for 16 hours.

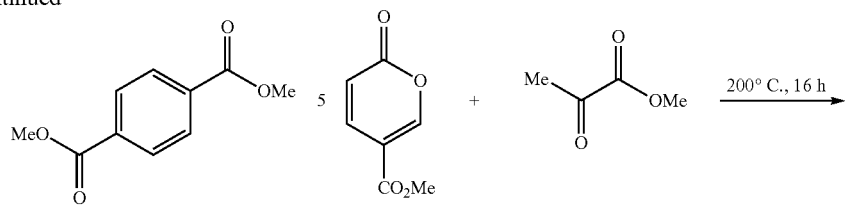

9 (95%)

Example 4

Synthesis of dimethyl terephthalate via methyl 2,2-dimethoxypropanoate

The experimental procedure to synthesize 9 was followed as described in Example 1; however, the reaction was maintained at 200° C. for 16 hours.

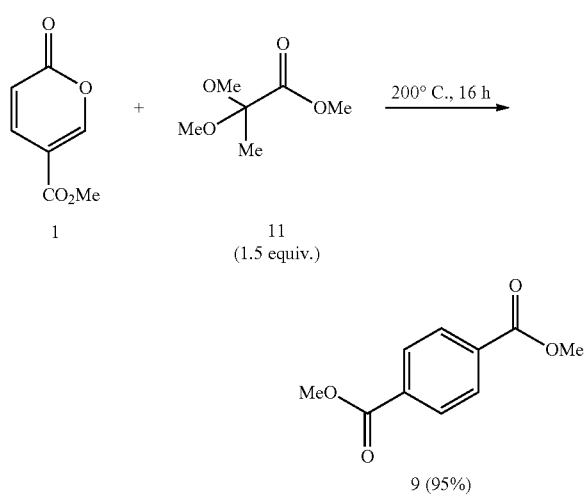

An additional experimental trial is as follows:

| Temperature (° C.) | Time (h) | Equivalents of 11 | Concentration (M) | Ratio of 9:11 |
|---|---|---|---|---|
| 150 | 1 | 1.0 | Neat | 1:2.69 |

Example 5

Synthesis of dimethyl terephthalate via methyl pyruvate

The experimental procedure to synthesize 9 was followed as described in Example 1; however, 3 equivalents of 12 were required and the reaction was maintained at 200° C. for 16 hours.

9 (59%)

An additional experimental trial is as follows:

| Temperature (° C.) | Time (h) | Equivalents of 12 | Concentration (M) | Ratio of 9:12 |
|---|---|---|---|---|
| 200 | 16 | 1.5 | Neat | 1:1 |

All patents, patent applications and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:
1. A method for the synthesis of a compound of formula (I):

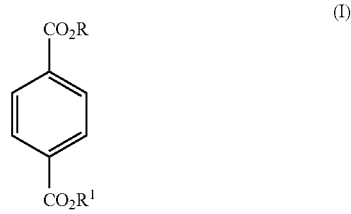

(I)

wherein R and $R^1$ are individually selected from H, alkyl, arylalkyl, cycloalkyl or cycloalkylalkyl comprising:
reacting a coumalate compound of formula (II):

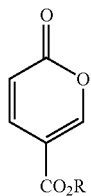

optionally in the presence of a solvent, with a captodative alkene of formula (III), (IV) or (V):

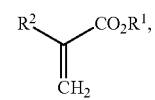

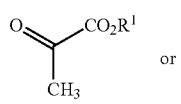

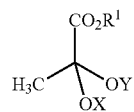

wherein $R^2$ is —OR, —SR, halo (F, Cl, Br, I), $(R)_2N$, RC(O)— or —O[Si($R^a$)($R^b$)($R^c$)] wherein each of $R^a$, $R^b$ or $R^c$ are individually selected from ($C_1$-$C_6$)alkyl, and wherein X and Y are individually R or $R^1$, or together are —$(CH_2)_n$—, wherein n is 2-3 and —$(CH_2)_n$— is optionally substituted with R, so as to yield a compound of formula (I).

2. The method of claim 1 wherein each of R, $R^1$, X or Y is ($C_1$-$C_4$)alkyl.

3. The method of claim 2 wherein each of R, $R^1$, X or Y is methyl.

4. The method of claim 3 wherein $R^a$, $R^b$ and $R^c$ are methyl.

5. The method of claim 4 where $R^2$ is methoxy.

6. The method of claim 1 that is carried out in the absence of solvent.

7. The method of claim 1 that is carried out at a molar ratio of III, IV or V to (II) of about 3:1.

8. The method of claim 7 wherein the reaction is carried out about 150-200° C.

9. The method of claim 8 wherein the reaction is carried out for 3-16 hours.

10. The method of claim 1 wherein the compound of formula I is dimethyl terephthalate.

11. The method of claim 1 which is carried out without a metal catalyst.

* * * * *